United States Patent [19]

Middleton et al.

[11] Patent Number: 4,459,427

[45] Date of Patent: Jul. 10, 1984

[54] PROCESS FOR THE CONVERSION OF AN ALKANE TO A MIXTURE OF AN ALCOHOL AND A KETONE

[75] Inventors: Anthony R. Middleton, Sunbury-on-Thames; David J. H. Smith, Camberley, both of England

[73] Assignee: The British Petroleum Company p.l.c., London, England

[21] Appl. No.: 436,785

[22] Filed: Oct. 26, 1982

[30] Foreign Application Priority Data

Oct. 31, 1981 [GB] United Kingdom ............... 8132870
Oct. 31, 1981 [GB] United Kingdom ............... 8132871

[51] Int. Cl.³ .............................................. C07C 45/27
[52] U.S. Cl. .................................. 568/342; 568/385; 568/836; 568/910
[58] Field of Search ............... 568/342, 385, 836, 910

[56] References Cited

U.S. PATENT DOCUMENTS 3,879,467  4/1975  Zajacek et al. ..................... 568/342

FOREIGN PATENT DOCUMENTS 760254   6/1971  Belgium ............................. 568/342
27937    5/1981  European Pat. Off. ............. 568/342
2400322  7/1974  Fed. Rep. of Germany ...... 568/342
735588   5/1980  U.S.S.R. ............................ 568/342

Primary Examiner—Werren B. Lone
Attorney, Agent, or Firm—Brooks, Haidt, Haffner & Delahunty

[57] ABSTRACT

A mixture of the alcohol and ketone derivatives of alkanes is produced by reacting the alkane with a hydrocarbyl hydroperoxide, eg t-butyl hydroperoxide, at ambient or elevated temperature and pressure in the presence as catalyst of an iron or manganese square planar complex having heterocyclic nitrogen-donor ligands, e.g. a porphyrin or phthalocyanine complex, which complex has either no axial ligands, eg the lower valency or cationic complex, or an axial ligand which is non-coordinating or weakly-coordinating.

7 Claims, No Drawings

PROCESS FOR THE CONVERSION OF AN ALKANE TO A MIXTURE OF AN ALCOHOL AND A KETONE

The present invention relates to a process for the conversion of non-activated alkanes to a mixture of their corresponding alcohol and ketone derivatives.

As the world's known oil reserves are being depleted at a faster rate than exploration provides new reserves, there is a growing search for alternative long-term sources of chemicals feedstock. Both coal, which is relatively abundant, and natural gases, eg methane and ethane, which are abundantly available and are in many cases currently flared off as an unwanted by-product of oil production, are coming under increasing scrutiny as potential chemicals feedstocks. One approach is to convert them to a mixture of carbon monoxide and hydrogen (synthesis gas) using well-known technology and thereafter to convert catalytically the synthesis gas into oxygenated hydrocarbons such as alcohols, acids, esters or aromatics.

A desirable objective is to eliminate the intermediate production of synthesis gas and convert paraffins directly into oxygenated hydrocarbons, such as alcohols and ketones.

The oxidation of cyclohexane to mixtures containing cyclohexanone and cyclohexanol is a well-known, competitive, large volume industrial process. In European patent application publication No. 0027937 there is disclosed an improved process for oxidising cyclohexane to produce a reaction mixture containing cyclohexyl hydroperoxide and decomposing the cyclohexyl hydroperoxide in the presence of starting cyclohexane to form a mixture containing cyclohexanone and cyclohexanol wherein the improvement comprises using in the oxidation step and/or the decomposition step as a catalyst a transition metal complex of certain 1,3-bis(-pyridylimino)-isoindolines. A feature of this process is that the participation of cyclohexane results in a higher conversion of cyclohexane to useful oxidation products than would be realised if the cyclohexane hydroperoxide decomposed by itself. Furthermore, D. Mansuy, J. F. Bartoli, J. Chottard and M. Lange in Angew. Chem. Int. Ed. Engl. 19 (1980) No. 11, pages 909/910 describe the hydroxylation of cyclohexane by alkyl hydroperoxides using as catalysts certain metalloporphyrins and in particular iron (111) and manganese (111) porphyrins in the form of Fe(TPP)(Cl) and Mn(TPP)Cl wherein (TPP) represents the tetraphenyl porphyrin moiety. Both of these compounds are characterised by a square planar structure with an axially protruding Cl ligand.

We have now found that the yield of hydroxylation products, ie alcohols and ketones, from a variety of non-activated paraffins can be substantially improved by using as catalyst an iron or manganese square planar complex with heterocyclic nitrogen-donor ligands having either no axial ligands or non-coordinating or weakly coordinating axial ligands.

Accordingly, the present invention provides a process for the conversion of alkanes into a mixture of their corresponding alcohol and ketone derivatives which process comprises reacting the alkane with a hydrocarbyl hydroperoxide at ambient or elevated temperature and pressure in the presence as catalyst of an iron or manganese square planar complex having heterocyclic nitrogen-donor ligands which complex has either no axial ligand or an axial ligand which is non-coordinating or weakly coordinating.

The alkane may suitably be a linear, branched or cyclic alkane and may be liquid or gaseous. Preferably the alkane is a $C_2$ to $C_{10}$ linear or branched alkane. Suitable alkanes include ethane, propane, butane, pentane, hexane, heptane, octane, nonane, decane and cyclohexane.

The hydrocarbyl group of the hydrocarbyl hydroperoxide may suitably be an alkyl, cycloalkyl, aryl or alkaryl group. Examples of suitable hydrocarbyl hydroperoxides include t-butyl hydroperoxide, cumyl hydroperoxide, cyclohexyl hydroperoxide and phenyl ethyl hydroperoxide, of which t-butyl hydroperoxide is preferred. Hydrocarbyl hydroperoxides may be prepared in known manner by oxidation of the corresponding alkane, for example t-butyl hydroperoxide may be prepared by the oxidation of isobutane. The molar ratio of hydrocarbyl hydroperoxide to the alkane reactant may suitably be varied over a wide range. For high utilisation of the hydroperoxide reactant low standing concentrations of the hydroperoxide are preferred.

As catalyst there is used an iron or manganese square planar complex with heterocyclic nitrogen donor ligands having either no axial ligands or non-coordinating or weakly coordinating axial ligands. Preferred iron and manganese square planar complexes are phthalocyanine and porphyrin complexes. Suitable complexes having no axial ligands are either neutral iron (11) and manganese (11) complexes eg Fe(11) (TPP) and Mn(11)(TPP) or iron (111) and manganese (111) cationic complexes, eg [Fe(111)(TPP)]+ and [Mn(111)(TPP)]+. The iron (11) and manganese (11) neutral complexes may be obtained by chemical reduction of the corresponding iron (111) and manganese (111) complexes, suitably by reaction with iron or zinc powder. Chemical reduction may be carried out either prior to or during the process of the invention. The iron (111) and manganese (111) cationic complexes may suitably be prepared by reacting an iron (111) or manganese (111) complex having an axial halide ligand, eg Fe(111)(TPP)Cl or Mn(111)(TPP)Cl, with, for example, silver salts of phosphorus hexafluoride, phosphorus hexachloride, antimony hexafluoride, antimony hexachloride, tetraphenylboron or tetrafluoroboron.

Weakly coordinating ligands may be defined as ligands having a coordinating power less than that of the chloride anion. Suitable examples of non-coordinating or weakly coordinating ligands are solvent molecules, eg tetrahydrofuran, and the anions derived from benzoic acid, boric acid and sulphuric acid. Solvent molecules may be incorporated during preparation of the complex in a solvent medium. Non-coordinating or weakly coordinating ligands may be incorporated 'in-situ' during the process of the invention using as catalyst an iron or manganese complex having a strongly coordinating axial ligand, eg the chloride anion, by addition of an acid having a noncoordinating or weakly coordinating anion, eg sulphuric acid, boric acid or benzoic acid. The addition of the acid leads to an improvement in the yield of hydroxylation products, which improvement is particularly marked using oxo-bridged porphyrins as catalyst. The amount of acid added may suitably be in the range from 1 to 25% by weight, based on the weight of alkane reactant.

The amount of catalyst present may suitably be in the range from 0.001 to 10%, preferably from 0.1 to 4% by weight, based on the weight of the reactants.

The reaction may be carried out in the presence or absence of a solvent. Suitable solvents include liquid hydrocarbons, such as benzene, and coordinating solvents, such as oxygenated hydrocarbons, eg tetrahydrofuran and acetone. The solvent may suitably be present in any desired proportions.

Although the reaction may suitably be carried out at ambient temperatures and pressures, elevated temperatures, eg up to about 250° C., and elevated pressures may be employed if desired. Using gaseous alkane feeds, elevated pressure is preferably employed. In operating the process of the invention it is preferred to maintain a low standing concentration of hydrocarbyl hydroperoxide relative to the alkane reactant. This may suitably be achieved by adding the hydroperoxide dropwise, whilst stirring the reactants.

The process may be carried out batchwise or continuously.

The process of the invention will now be further illustrated by reference to the following Examples. In the Examples the abbreviation "(TPP)" represents "tetraphenylporphyrin" and "(PC)" represents phthalocyanine.

EXAMPLE 1 t-Butyl hydroperoxide (5.4M in t-butanol/water) (10 cm$^3$) was added dropwise over 0.5 h to a stirred solution of Fe(11)(TPP).2THF (0.1 g) in benzene (20 cm$^3$) and cyclohexane (20 cm$^3$) at room temperature. The mixture was stirred for a further hour and then analysed by GLC.

EXAMPLE 2

Example 1 was repeated except that t-butyl hydroperoxide was replaced by cumyl hydroperoxide.

EXAMPLE 3

Example 1 was repeated except that cyclohexane was replaced by n-hexane.

EXAMPLE 4

Example 1 was repeated except that cyclohexane was replaced by n-pentane.

Comparison Test 1

Example 1 was repeated except that the Fe(11)(TPP).2THF catalyst was replaced by the corresponding Fe(111) complx, Fe(111)(TPP)Cl.

The results of Examples 1 to 4 and Comparison Test 1 are given in Table 1.

It can be seen from the results of Example 1 and Comparison Test 1 in Table 1 that the use of the Fe(11) complex (no axial ligand) in place of the Fe(111) complex (axial Cl ligand) leads to increased yields of useful products.

EXAMPLE 5 t-Butyl hydroperoxide (5.4M in t-butanol/water) (10 cm$^3$) was added dropwise over 0.5 h to a stirred solution of Fe(111)(TPP)Cl (0.1 g) in cyclohexane (20 cm$^3$), which contained boric acid (0.5 g, 0.008M). The solution was stirred for a further hour and then analysed by G.L.C.

EXAMPLE 6

Example 5 was repeated except that the catalyst and boric acid were initially dissolved in benzene (20 cm$^3$). Similar results were obtained.

EXAMPLE 7

Example 5 was repeated except that the catalyst and boric acid were initially dissolved in acetone (20 cm$^3$). Similar results were obtained.

EXAMPLE 8

Example 5 was repeated except that the boric acid was replaced by sulphuric acid.

TABLE 1

| | REACTANTS | | | | PRODUCTS (YIELD %) | | | | | |
|---|---|---|---|---|---|---|---|---|---|---|
| Example | Alkane | Catalyst | Hydroperoxide | | | | | | | |
| 1 | cyclohexane | Fe (II)(TPP).2THF | t-butyl | t-butanol | (95) | cyclohexanol | (18) | cyclohexanone | (35) |
| 2 | cyclohexane | " | cumyl | cumyl alcohol | (80) | cyclohexanol | (24) | cyclohexanone | (24) |
| 3 | n-hexane | " | t-butyl | t-butanol | (96) | mixed alcohols* | (9) | mixed ketones* | (15) |
| 4 | n-pentane | " | " | t-butanol | (99) | mixed alcohols* | (10) | mixed ketones* | (16) |
| Comp. Test. | cyclohexane | Fe(III)(TPP)Cl | t-butyl | t-butanol | (95) | cyclohexanol | (14) | cyclohexanone | (15) |

*Mixtures of alcohols and ketones are produced, which reflect a distinct preference for secondary products with only small yields of primary alcohols being observed.

EXAMPLE 9

Example 5 was repeated except that the boric acid was replaced by benzoic acid.

Comparison Test 2

Example 1 was repeated except that no acid was present.

EXAMPLE 10

Example 8 was repeated except Fe(TPP)Cl was replaced by the oxobridged dimer [Fe(TPP)]$_2$O (0.1 g).

EXAMPLE 11

Example 9 was repeated except Fe(TPP)Cl was replaced by [Fe(TPP)]$_2$O (0.1 g).

Comparison Test 3

Example 10 was repeated except that no acid was present. The results of Examples 5–11 and Comparison Tests 2 and 3 are given in Table 2.

TABLE 2

| Example | Catalyst | Acid | t-butanol (%) | cyclohexanol (%) | cyclohexanol (%) |
|---|---|---|---|---|---|
| Comp. Test 2 | Fe(TPP)Cl | — | 95 | 14 | 15 |
| Comp. Test 3 | [Fe(TPP)]$_2$O | — | 94 | 10 | 10 |
| Comp. Test 5 | Fe(TPP)Cl | boric | 95 | 17 | 22 |
| Comp. Test 8 | Fe(TPP)Cl | sulphuric | 87 | 16 | 23 |
| Comp. Test 9 | Fe(TPP)Cl | benzoic | 85 | 8 | 23 |
| Comp. | [Fe(TPP)]$_2$O | sulphuric | 86 | 16 | 24 |

TABLE 2-continued

| Example | Catalyst | Acid | t-but-anol (%) | cyclo-hexanol (%) | cyclo-hexanol (%) |
|---|---|---|---|---|---|
| Test 10 Comp. Test 11 | [Fe(TPP)]$_2$O | benzoic | 86 | 17 | 18 |

The results presented in Table 2 demonstrate the improvement in yield obtained by the addition of acids having either non-coordinating or weakly-coordinating anions to hydroxylation reactions catalysed by Fe(III)(TPP)Cl and [Fe(TPP)]$_2$O, complexes having strongly coordinating axial ligands.

EXAMPLE 12

Example 1 was repeated except that Fe(II)(TPP).2 THF was replaced by Mn(II)(TPP).

EXAMPLE 13

Example 9 was repeated except Fe(TPP)Cl was replaced by Mn(TPP)Cl.

Comparison Test 4

Example 1 was repeated except that Fe(II)(TPP).2THF was replaced by Mn(TPP)Cl (0.1 g).

The results of Examples 12 and 13 and Comparison Test 4 are given in Table 3.

TABLE 3

| Example | Catalyst | t-but-anol (%) | cyclo-hexanol (%) | cyclo-hexanone (%) |
|---|---|---|---|---|
| 12 | Mn(II) (TPP) | 88 | 9 | 18 |
| 13 | Mn(III) (TPP)Cl/ benzoic acid | 85 | 7 | 14 |
| Comp. Test 4 | Mn(III) (TPP)Cl | 85 | 6 | 11 |

The results presented in Table 3 demonstrate the improvement in yield obtained by the use of the MnII complex (no axial ligand) or by the addition of benzoic acid (weakly coordinate ligand) in place of the MuIII complex (axial Cl ligand).

EXAMPLE 14 t-butyl hydroperoxide (2.25M in t-buOH) (20 cm$^3$) was added at a rate of 30 cm$^3$hr$^{-1}$ to a stirred solution of [Fe(III)(TPP)]+PF$_6^-$ (0.1 g) in benzene (20 cm$^3$) and cyclohexane (20 cm$^3$) at 40° C. The mixture was stirred for a further hour and then analysed by GLC.

Comparison Test 5

Example 14 was repeated except [Fe(III)(TPP)]+PF$_6^-$ was replaced by Fe(TPP)Cl (0.1 g).

The results of Example 14 and Comparison Test 5 are given in Table 4.

TABLE 4

| Example | Catalyst | t-but-anol (%) | cyclo-hexanol (%) | cyclo-hexanone (%) |
|---|---|---|---|---|
| 14 | [Fe(TPP)]+PF$_6^-$ | 88 | 21 | 23 |
| Comp. Test 5 | Fe(TPP)Cl | 86 | 15 | 17 |

The results presented in Table 4 demonstrate the improvement in yield obtained by the use of salts containing no axial ligands as compared with those containing axial ligands.

EXAMPLE 15

Example 14 was repeated except [Fe(TPP)]+PF$_6^-$ was replaced by Fe(PC) (0.1 g).

EXAMPLE 16

Example 14 was repeated except [Fe(TPP)]+PF$_6^-$ was replaced by Mn(PC) (0.1 g).

Comparison Test 6

Example 14 was repeated except [Fe(TPP)]+PF$_6^-$ was replaced by Co(PC) (0.1 g).

Comparison Test 7

Example 14 was repeated except [Fe(TPP)]+PF$_6^-$ was replaced by Cu(PC) (0.1 g).

The results of Examples 15 and 16 and Comparison Tests 6 and 7 are given in Table 5.

TABLE 5

| Example | Catalyst | t-but-anol (%) | cyclohexanol (%) | cyclohexanone (%) |
|---|---|---|---|---|
| 15 | Fe(PC) | 92 | 14 | 13 |
| 16 | Mn(PC) | 87 | 11 | 14 |
| Comp. Test 6 | Co(PC) | 45 | 6 | 5 |
| Comp. Test 7 | Cu(PC) | <5 | 1 | 1 |

The results presented in Table 5 demonstrate the advantage of using iron and manganese phthalocyanine complexes without axial ligands over other metal phthyalocyanine complexes.

We claim:

1. A process for the conversion of C$_2$ to C$_{10}$ alkanes into a mixture of their corresponding alcohol and ketone derivatives which process comprises reacting the alkane with a hydrocarbyl hydroperoxide at ambient or elevated temperature and pressure in the presence as catalyst of an iron or manganese square planar complex having heterocylic nitrogen donor ligands, which complex has either no axial ligand or an axial ligand which is non-coordinating or weakly coordinating.

2. A process according to claim 1 wherein the hydrocarbyl hydroperoxide is t-butyl hydroperoxide.

3. A process according to claim 1 wherein the complex is a phthalocyanine or a porphyrin complex.

4. A process according to claim 1 wherein the complex has no axial ligands and is an iron (11) or manganese (11) complex.

5. A process according to claim 1 wherein the complex has no axial ligands and is an iron (111) or manganese (111) cationic complex.

6. A process according to claim 1 wherein the complex has a non-coordinating or weakly coordinating axial ligand.

7. A process according to claim 1 wherein the complex is formed 'in-situ' from a complex having a strongly coordinating axial ligand by the addition of an acid selected from sulphuric acid, boric acid and benzoic acid.

* * * * *